(12) United States Patent
Gerber-Siff et al.

(10) Patent No.: US 10,641,756 B2
(45) Date of Patent: May 5, 2020

(54) AUTOMATED SOIL MEASUREMENT

(71) Applicant: WINFIELD SOLUTIONS, LLC, Shoreview, MN (US)

(72) Inventors: Bevan Gerber-Siff, San Francisco, CA (US); Justin White, Palo Alto, CA (US); Stephen Prouty, San Jose, CA (US); Robert Tirrell, Mountain View, CA (US); Michael Preiner, Palo Alto, CA (US); Nicholas Koshnick, Palo Alto, CA (US)

(73) Assignee: WINFIELD SOLUTIONS, LLC, Arden Hills, MN (US)

( * ) Notice: Subject to any disclaimer, the term of this patent is extended or adjusted under 35 U.S.C. 154(b) by 140 days.

(21) Appl. No.: 15/832,512

(22) Filed: Dec. 5, 2017

(65) Prior Publication Data

US 2018/0224419 A1 Aug. 9, 2018

Related U.S. Application Data

(63) Continuation of application No. 14/866,391, filed on Sep. 25, 2015, now Pat. No. 9,863,925, which is a (Continued)

(51) Int. Cl.
*G01N 33/24* (2006.01)
*G01N 1/40* (2006.01)
(Continued)

(52) U.S. Cl.
CPC .......... *G01N 33/24* (2013.01); *G01N 1/4077* (2013.01); *B01D 29/00* (2013.01);
(Continued)

(58) Field of Classification Search
CPC .... G01N 33/24; G01N 1/38; G01N 2033/245; G01N 21/00; G01N 21/31; G01N 21/3563; G01N 21/3577
See application file for complete search history.

(56) References Cited

U.S. PATENT DOCUMENTS 350,181 A * 10/1886 Ackerson ............... B01D 35/30
210/238
1,840,100 A 1/1932 Jacobsen
(Continued)

FOREIGN PATENT DOCUMENTS

CA 2375891 A1 9/2003
EP 0802406 A2 10/1997
(Continued)

OTHER PUBLICATIONS

Matala BioSteps 10 Gravity Discharge Filter, Matala USA, available on the internet archive, Dec. 6, 2011. (Year: 2011).*
(Continued)

*Primary Examiner* — David A Rogers
(74) *Attorney, Agent, or Firm* — Dorsey & Whitney LLP

(57) ABSTRACT

A filtration system for a soil analysis device and methods of pressure filtration and automated cleaning are disclosed for generating filtrate used in measuring characteristics of a soil sample and preparing the filtration system for repeated measurements. A mixing chamber combines a soil sample and an extractant into a liquid mixture. The filtration system receives and pressure filters the liquid mixture to quickly generate filtrate used to measure characteristics of the sample. The filtrate is passed to a measurement cell for analysis. Once the analysis is complete, the filtration system performs a cleaning process in preparation to receive a subsequent liquid mixture from another soil sample.

20 Claims, 9 Drawing Sheets

Related U.S. Application Data continuation of application No. 13/794,331, filed on Mar. 11, 2013, now Pat. No. 9,146,223.

(60) Provisional application No. 61/679,570, filed on Aug. 3, 2012.

(51) Int. Cl.
   *B01D 29/00* (2006.01)
   *G01N 35/00* (2006.01)
   *G01N 35/10* (2006.01)

(52) U.S. Cl.
   CPC . *G01N 35/1095* (2013.01); *G01N 2001/4088* (2013.01); *G01N 2033/245* (2013.01); *G01N 2035/00475* (2013.01)

(56) References Cited

U.S. PATENT DOCUMENTS

| | | | |
|---|---|---|---|
| 2,759,557 A * | 8/1956 | Gordon | E03F 5/16 210/306 |
| 3,193,555 A | 7/1965 | Shavel et al. | |
| 3,573,470 A | 4/1971 | Haley | |
| 3,861,802 A | 1/1975 | Belmear | |
| 4,266,878 A | 5/1981 | Auer | |
| 4,389,237 A | 6/1983 | Patchett et al. | |
| 4,940,539 A * | 7/1990 | Weber | B01D 17/047 210/149 |
| 4,997,281 A | 3/1991 | Stark | |
| 5,067,616 A | 11/1991 | Plester et al. | |
| 5,114,586 A * | 5/1992 | Humphrey | C02F 1/006 210/104 |
| 5,117,370 A | 5/1992 | Decello et al. | |
| 5,155,545 A | 10/1992 | Rinke | |
| 5,223,715 A | 6/1993 | Taylor | |
| 5,247,177 A | 9/1993 | Goldberg et al. | |
| 5,526,705 A | 6/1996 | Skotnikov et al. | |
| 5,621,213 A | 4/1997 | Barshad | |
| 5,630,987 A | 5/1997 | Briggs et al. | |
| 5,637,218 A * | 6/1997 | Kickuth | C02F 3/046 210/170.08 |
| 5,753,109 A | 5/1998 | Looney et al. | |
| 5,768,128 A | 6/1998 | Thompson et al. | |
| 5,887,491 A | 3/1999 | Monson et al. | |
| 5,974,889 A | 11/1999 | Trantow | |
| 5,974,899 A | 11/1999 | Hanks | |
| 6,015,498 A | 1/2000 | Gleizes | |
| 6,048,456 A * | 4/2000 | Palmer | B01D 24/001 210/282 |
| 6,221,246 B1 * | 4/2001 | Shums | B01D 29/15 210/248 |
| 6,287,358 B1 | 9/2001 | Mason et al. | |
| 6,324,922 B1 | 12/2001 | Hanks | |
| 6,324,924 B1 | 12/2001 | Peterson | |
| 6,356,830 B1 | 3/2002 | Adamchuk et al. | |
| 6,596,996 B1 | 7/2003 | Stone et al. | |
| 6,831,746 B2 | 12/2004 | Cassidy et al. | |
| 6,931,950 B2 | 8/2005 | Malachowski et al. | |
| 6,937,939 B1 | 8/2005 | Shibusawa et al. | |
| 7,135,871 B1 | 11/2006 | Pelletier | |
| 7,188,450 B2 | 3/2007 | Raun et al. | |
| 7,216,555 B2 | 5/2007 | Drummond et al. | |
| D591,825 S * | 5/2009 | Quintel | D23/209 |
| 7,556,773 B2 | 7/2009 | Horan et al. | |
| 8,034,307 B2 | 10/2011 | Hanlon | |
| 8,144,319 B2 | 3/2012 | Preiner et al. | |
| 8,282,818 B1 * | 10/2012 | Dobie | C02F 3/06 210/151 |
| 8,325,336 B2 | 12/2012 | Preiner et al. | |
| 8,446,586 B2 | 5/2013 | Wu et al. | |
| 8,472,023 B2 | 6/2013 | Preiner et al. | |
| 8,472,024 B2 | 6/2013 | Preiner et al. | |
| 8,477,295 B2 | 7/2013 | Preiner et al. | |
| 8,767,194 B2 | 7/2014 | Preiner et al. | |
| 9,146,223 B1 | 9/2015 | Gerber-Siff et al. | |
| 9,255,878 B2 | 2/2016 | Preiner et al. | |
| 9,291,545 B1 | 3/2016 | White et al. | |
| 9,714,901 B2 | 7/2017 | Preiner et al. | |
| 9,739,693 B2 | 8/2017 | White et al. | |
| 9,863,925 B2 | 1/2018 | Gerber-siff et al. | |
| 10,168,260 B2 | 1/2019 | White et al. | |
| 2001/0019026 A1 * | 9/2001 | Berg | B01D 17/00 210/170.08 |
| 2003/0010691 A1 | 1/2003 | Broussard | |
| 2003/0025909 A1 | 2/2003 | Hallstadius | |
| 2003/0063276 A1 | 4/2003 | Sjödin | |
| 2003/0097947 A1 | 5/2003 | Caruthers et al. | |
| 2003/0142301 A1 | 7/2003 | Coleman et al. | |
| 2003/0205525 A1 | 11/2003 | Severin | |
| 2003/0219057 A1 | 11/2003 | Govorkov et al. | |
| 2004/0009610 A1 | 1/2004 | Schabron et al. | |
| 2004/0183235 A1 | 9/2004 | Dairoku et al. | |
| 2004/0217048 A1 * | 11/2004 | Kirsgalvis | B01D 35/30 210/435 |
| 2004/0251189 A1 * | 12/2004 | Humphrey | C02F 3/02 210/220 |
| 2005/0042623 A1 | 2/2005 | Ault-riche et al. | |
| 2006/0088939 A1 | 4/2006 | Rajendram | |
| 2006/0090219 A1 | 4/2006 | Kisaka et al. | |
| 2006/0141636 A1 | 6/2006 | Steggles et al. | |
| 2007/0013908 A1 | 1/2007 | Lee et al. | |
| 2007/0073491 A1 | 3/2007 | Jahn et al. | |
| 2007/0122185 A1 | 5/2007 | Yamazaki et al. | |
| 2007/0138401 A1 | 6/2007 | Tokhtuev et al. | |
| 2007/0141232 A1 | 6/2007 | Tochterman et al. | |
| 2007/0228269 A1 | 10/2007 | Miller et al. | |
| 2007/0292308 A1 | 12/2007 | Horan et al. | |
| 2008/0050762 A1 | 2/2008 | Corey et al. | |
| 2008/0128609 A1 | 6/2008 | Miller et al. | |
| 2008/0194033 A1 | 8/2008 | Golitz | |
| 2008/0198381 A1 | 8/2008 | Heggs et al. | |
| 2008/0218734 A1 | 9/2008 | Higashi et al. | |
| 2008/0291455 A1 | 11/2008 | Holland | |
| 2009/0166520 A1 | 7/2009 | Tuli et al. | |
| 2010/0003760 A1 | 1/2010 | Agrawal et al. | |
| 2010/0176050 A1 * | 7/2010 | Mori | B01D 46/0039 210/435 |
| 2010/0270220 A1 * | 10/2010 | Juhere | B65D 88/06 210/170.08 |
| 2011/0054864 A1 | 3/2011 | Lundstedt et al. | |
| 2011/0125477 A1 | 5/2011 | Lightner et al. | |
| 2011/0242530 A1 | 10/2011 | Tuli et al. | |
| 2012/0047988 A1 | 3/2012 | Mehus et al. | |
| 2016/0247009 A1 | 8/2016 | Lu | |
| 2017/0322148 A1 | 11/2017 | Preiner et al. | |
| 2019/0120737 A1 | 4/2019 | White et al. | |

FOREIGN PATENT DOCUMENTS

| | | |
|---|---|---|
| GB | 1202236 A | 8/1970 |
| JP | 55035257 | 3/1980 |
| JP | 2002527740 A | 8/2002 |
| JP | 2005147811 A | 6/2005 |
| JP | 2006145529 A | 6/2006 |
| JP | 2012526289 A | 10/2012 |
| WO | 0043751 A1 | 7/2000 |

OTHER PUBLICATIONS

Biosteps 10, Matala Water Technology Co., date unknown.*
"2007", Census of Agriculture Report Online, http://vvwv,ragcensus.usda.gov, Feb. 2009, pp. 1-739.
"Dramatic Increases in Corn and Soybean Costs in 2009", Farm Economics: Facts and Opinions Online, http://www.farmdoc.illinois.edu/manage/newsletters/fefo08_13/fefo08_13.htrnl, Jul. 11, 2008, 4 pages.
"Grand Challenges for Engineering", National Academy of Engineering of the Natural Sciences Online from Dec. 1, 2010, http://vvvww.engineeringchallenges.org, 2009.
"PCT International Search Report and Written Opinion", PCT Application No. PCT/US2010/034048, dated Jul. 1, 2010, 8 pages.

(56) References Cited

OTHER PUBLICATIONS

"PCT International Search Report and Written Opinion", PCT Application No. PCT/US2010/034053, dated Jul. 1, 2010, 9 pages.
"World Greenhouse Gas Emissions by Sector", UNEP/GRID—Arendal from the internet http://maps.grida.no/go/graphic/world-green-house-gasemis-sions-by-sector, 2008.
Adamchuk, V.I. et al., "On-the-Go Mapping of Soil Properties Using Ion-Selective Electrodes", In: Stafford, JV., Werner, A. (Ed.), Precision Agriculture, 2003.
Bouvier, J-C et al., "On-Line Monitoring of Nitrate and Nitrite by UV Spectrophotometry in a SBR Process Used for the Treatment of Industrial Wastewaters", International Journal of Chemical Reactor Engineering, 2008, 21 pages vol. 6.
Bravo, M et al., "Nitrate Determination in Chilean Caliche Samples by UV-Visible Absorbance Measurements and Multivariate Calibration", J. Ghil. Chem. Soc.,, 2009, pp. 93-98, vol. 54, No. 1.
Crumpton, W. G. et al., "Nitrate and Organic N Analyses with Second-Derivative Spectroscopy", Limnol. Oceanogr., 1992, pp. 907-913, vol. 37, No. 4.
Dress, P. et al., "Water-Core Waveguide for Pollution Measurements in the Deep Ultraviolet", Applied Optics, Jul. 20, 1998, pp. 4991-4667, vol. 37, No. 21.
Ferree, M. A. et al., "Evaluation of a Second Derivative UV/Visible Spectroscopy Technique for Nitrate and Total Nitrogen Analysis of Wastewater Samples", Wat. Res.,, 2001, pp. 327-332, vol. 3, No. 1.
Jahn, B. R. et al., "Mind-infrared Spectroscopic Determination of Soil Nitrate Content", Biosystems Engineering, 2006, pp. 505-515, vol. 94, No. 4.
Jannasch, H. W. et al., "The Land/Ocean Biogeochemical Observatory: A Robust Networked Mooring System for Continuously Monitoring Complex Biogeochemical Cycles in Estuaries", Limnology and Oceanography: Methods, 2008, pp. 263-276, vol. 6.
Japan Patent Office, "Office Action" in application No. 2015-231171, dated Nov. 8, 2016, 4 pages.
Japan Patent Office, "Search Report" in application No. 2015-231170, dated Nov. 8, 2016, 4 pages.
Johnson, K. S. et al., "In Situ Ultraviolet Spectrophotometry for High Resolution and Long-Term Monitoring of Nitrate, Bromide and Bisulfide in the Ocean", Deep-Sea Research Part I,, 2002, pp. 1291-1305, vol. 49.
Karlsson, M. et al., "Determination of Nitrate in Municipal Waste Water by UV Spectroscopy", Analytica Chimica Acta, 1995, pp. 107-113, vol. 312.
Kim, H. J. et al., "Evaluation of Nitrate and Potassium Ion-Selective Membranes for Soil Macronutrient Sensing", Transactions of the ASABE, 2006, pp. 597-606 vol. 49, No. 3.
Lambert, D. et al., "Precision Agriculture Profitability Review", www.agriculture.purdue.edu/ssmc/, Sep. 15, 2000, pp. 1-154.
Ocean Optics, Inc., , "Maya2000 Pro Delivers Serious Performance", Retrieved online Nov. 30, 2010, www.oceanoptics.corn/products/maya. asp>,, 1989-2010, 2 pages.
Price, R. R. et al., "Rapid Nitrate Analysis of Soil Cores Using ISFETs", Transactions of the ASAE, 2003, pp. 1-10 vol. 46 No. 3.
Pruitt, P. , "Nitrate Measurement in Less Than 30 Seconds", Water Environment Laboratory, Feb./Mar. 2009, pp. 1-15, vol. 16, No. 1.
Randall, G. W. et al., "Nitrate Nitrogen in Surface Waters as Influenced by Climatic Conditions and Agricultural Practices", Journal of Environmental Quality, 2003, pp. 337-344 vol. 30.
Ratako, A. et al., "Micro- and Mini-Nitrate Sensors for Monitoring of Soils, Groundwater and Aquatic Systems", Center for Embedded Network Sensing, May 12, 2009, 3 pages.
Selk, G. E. et al., "Comparing the Accuracy of the Cardy Portable Nitrate Meter with Laboratory Analysis of Nitrate Concentrations in Summer Annual Forages", Online at http:/iwww.ansiokstate.edu/research/2004rr/02/0-2htm>, 2004, 4 pages.
Sempere, A. et al., "Simple Determination of Nitrate in Soils by Second-Derivative Spectroscopy", Journal of Soil Science, 1993, pp. 633-639, vol. 44.
Sethuramasamyraja, B. et al., "Agitated soil measurement method for integrated on-the-go mapping of soil ph, potas,sium and nitrate contents", Computers and Electronics in Agriculture, 2008, 60:212-225.
Sibley, K. J. et al., "Field-Scale Validation of an Automated Soil Nitrate Extraction and Measurement System", Precision Agriculture, 2009, pp. 162-174 vol. 10.
Simonsson, Magnus et al., "Estimating Nitrate, Dissolved Organic Carbon and DOC Fractions in Forest Floor leachates Using Ultraviolet Absorbance Spectra and Multivariate Analysis", Jan. 2005.
Stark, P. C. et al., "Pre-PCR DNA Quantitation of Soil and Sediment Samples: Method Development and Instrument Design", Soil Biology and Biochemistry, 2000, pp. 1101-1110 vol. 32.
Stellarnet, Inc., , "EPP2000-HR High Resolution Miniature Spectrometers", Online, WV\Nv.stellarnet-inc.com/products_spectrometers_EPP2000HR.htm>, 2010, 2 pages.
The Nitrate Elimination Company, Inc. N. , "Soil Nitrate Test Kit Instructions", Lake Linden, MI Online www.nitrate.com/sntklOOseries.pdf>, 2009, 2 pages.
Thomas, O. et al., "Ultraviolet Multiwavelength Absorptiometry (UVMA) for the Examination of Natural Waters and Wastewaters Part I: General Considerations", Fresenius' Journal of Analytical Chemistry, 1993, pp. 234-237, vol. 338.
Thomas, O. et al., "Ultraviolet Multiwavelength Absorptiometry (UVMA) for the Examination of Natural Waters and Wastewaters, Part II. Determination of Nitrate", Fresenius' Journal of Analytical Chemistry, 1990, pp. 238-240, vol. 338.
Tuli, A. et al., "In Situ Monitoring of Soil Solution Nitrate: Proof of Concept", SSSAJ, Mar./Apr. 2009, pp. 501-509, vol. 73, No. 2.
Weishaar, J. L. et al., "Evaluation of Specific Ultraviolet Absorbance as an Indicator of the Chemical Composition and Reactivity of Dissolved Organic Carbon", Environmental Science and Technology, 2003, pp. 4702-4708 vol. 37 No. 20.
Yamaki, Atsushi , "A Rapid UV Absorption Methods for Determination of Nitrate un Soil Extracts", Japanese Journal of Soil Science and Plant Nutrition, Apr. 5, 2003, pp. 195-197 vol. 74, No. 2.
Yao, H. et al., "Hyperspectral Image Feature Extraction and Classification for Soil Nutrient Mapping", Precision Agriculture: Papers from the 4th European Conference on Precision Agriculture, Berlin, Germany, Jun. 15-19, 2003, p. 216.

\* cited by examiner

AUTOMATED SOIL MEASUREMENT

CROSS REFERENCE TO RELATED APPLICATIONS

This application is a continuation of U.S. patent application Ser. No. 14/866,391 filed Sep. 25, 2015, issued as U.S. Pat. No. 9,863,925 on Jan. 9, 2018, which is a continuation of U.S. application Ser. No. 13/794,331, filed Mar. 11, 2013, issued as U.S. Pat. No. 9,146,223 on Sep. 29, 2015, which claims priority to U.S. Provisional Application No. 61/679,570, filed on Aug. 3, 2012, the entire contents of all are hereby incorporated by reference for all purposes as if fully set forth herein.

BACKGROUND

1. Field of Art

The present invention generally relates to soil measurement and testing, and more specifically, filtration of a soil-extractant mixture.

2. Description of the Related Art

Nutrient levels in soil have significant spatial and temporal variations. Accordingly, there has been significant effort placed into development of local nutrient management schemes, often referred to as "precision agriculture," addressing nutrient level variation. Local nutrient management increases agricultural efficiency while reducing its environmental impact by allowing growers to locally apply nutrients where needed. Increases in nutrient costs and a growing awareness of the environmental consequences of current agriculture practices have made improvements in agricultural efficiency and environmental impact increasingly important.

For example, fertilizer inputs are a large fraction of agricultural input costs and prices of nutrient input have almost doubled in recent years, increasing concern about future price fluctuations among growers. Meanwhile, in addition to long-standing concerns about the effect of fertilizers on water quality, greenhouse gas emissions caused by nitrogen-based fertilizers have become an increasing concern. For example, it is estimated that N2O emissions caused by fertilizer volatilization are responsible for 5-10% of the forcing for global warming. Thus the ability to optimize the use of fertilizer inputs, and nitrogen-based fertilizers in particular, is increasingly recognized as a vital component of environmental sustainability. As a result of these factors, there is a rapidly growing interest in more efficient nutrient management.

Local measurement of soil nutrient levels is a significant component of local nutrient management scheme. However, conventional methods for locally measuring soil nutrient levels have limited the effectiveness of existing local nutrient management schemes. Conventionally, capturing a number of samples/acre at the appropriate time to make effective decisions is often prohibitively time consuming and expensive. For example, lettuce growers in certain area typically plant several crop cycles each year, and have a five day window between harvesting and planting the next crop. Logistically, this results in a very small time window, 1-2 days, in which to sample the field and apply fertilizer. This short time frame prevents use of standard laboratory-based soil testing, which often takes 1-2 weeks to provide a result. Consequently, growers typically make decisions on fertilizer application based on historical analysis, instead of on current soil conditions.

As another example, in-season nitrogen management in corn-growing regions is often difficult because of the slow turnaround time of laboratory-based soil testing. Extending the time when corn growers are able to measure soil nitrogen levels would allow corn growers to test fields before their last application of fertilizer. This enables corn growers to test fields later in the growing season and implement nitrogen management practices. Further, allowing growers to promptly retest fields, such as retesting after a rain, allows growers to adopt more efficient nitrogen management practices. Additionally, laboratory-based soil measurement costs scale directly with the number of samples, making it prohibitively expensive to sample at high grid densities. Thus, the development of a fast, simple, and inexpensive soil would expand the benefits of precision agriculture.

Additionally, standard laboratory-based tests are relatively slow and expensive. For example, a traditional laboratory-based test may use a filtration system that incorporates a filter that operates using the force of gravity. For example, gravity acts on a liquid mixture to generate filtrate for a measurement. This process is not only tedious but requires frequent replacement of filters, ideally a new filter for each sample processed. Labs may speed up these measurements by creating a vacuum on the filtrate side of the filter to generate a negative pressure differential to increase the rate of filtrate generation. Such methods are often used in controlled lab environments with specialized and fragile lab equipment such as Buchner flasks with a vacuum pump and the like. Such setups are impractical for use in the field.

Accordingly, there have thus been numerous efforts to develop various other fast soil nutrient detection tools for use in the field. Technologies used include mid-infrared (mid-IR) spectroscopy, ion-selective electrodes, and chemical-reaction based strip tests. However, the use of each method has suffered from some combination of expense, low accuracy, stringent calibration requirements or difficulty of use.

Accordingly, a rapid and economical system for soil analysis that does not require a controlled lab environment could provide more accurate and timely nutrient management recommendations which improve agricultural efficiency.

SUMMARY

A soil analysis device provides the ability to process a soil sample and analyze the processed soil sample to identify characteristics of the soil sample. For example, a soil analysis device combines a soil sample with an extractant, such as water, to produce a liquid mixture (or slurry). A portion of the slurry is exposed to a broad-band light source, with wavelengths varying from ultraviolet to visible to near-infrared, to generate an attenuation spectrum identifying the attenuation of different wavelengths of the light by the slurry. The attenuation spectrum is analyzed to determine characteristics of the soil sample. For example, peaks in the attenuation spectrum are analyzed to identify nutrients present in the soil sample. Such measurements provide an ideal analysis of soil properties like nitrogen concentration.

Embodiments of the soil analysis device described herein further provide the ability to process soil samples and perform such measurements with a high degree of accuracy and precision outside of a laboratory environment, such as at an agriculture retailer's office or a mobile trailer in the field. In one embodiment, the soil analysis device comprises a mixing chamber for generating the slurry, a filtration system for filtering unwanted particulate from the slurry to generate filtrate, and a measurement cell for analyzing the filtrate.

The speed of filtration and reliability in producing repeatable samples of slurry for measurements may be increased through pressure filtering in a sealed, self cleaning filtration system. An embodiment of the filtration system includes a slurry chamber for receiving the slurry from the mixing chamber. A filter separates the slurry chamber from a filtrate chamber and may be oriented in a substantially vertical orientation. Perforations in the filter allow filtered slurry (filtrate) to pass from the slurry chamber, through the perforations in the filter, into a filtrate chamber that collects filtrate for soil measurements.

To pressure filter a liquid mixture, the slurry chamber receives a volume of slurry from the mixing chamber sufficient to cover the perforations of the filter. In some embodiments, a valve coupled to the slurry chamber may release trapped air in the chamber as the liquid mixture is introduced. An air source pressurizes the slurry chamber which causes the filtration system to quickly generate a volume of filtrate by forcing the slurry through the filter. In other words, pressurization of the slurry chamber pressure filters the volume of slurry at a greater rate than otherwise possible, until the perforations are exposed and the pressure between the chambers is equalized. Depending on the embodiment, the air source may be coupled to the valve, utilize a second valve coupled to the slurry chamber, and/or pressurize the liquid mixture within the mixing chamber coupled to the slurry chamber. Once enough filtrate is generated for a measurement, or a measurement performed during filtration is complete, a drain of the slurry chamber may be opened to drain any remaining slurry.

In some embodiments, a compressor of the air source may be coupled to the filtrate chamber to create a vacuum. The vacuum may be generated in the filtrate chamber to evacuate air from the filter assembly In one embodiment, the vacuum is generated in the filtrate chamber to evacuate air in the filter assembly. The evacuation of air aids in quickly filling the slurry chamber of the filtration system. Once the slurry chamber is filled, the vacuum may be turned off and pressure in the slurry chamber is used to push the liquid mixture through the filter to create filtrate. In alternate embodiments, the generator may remain on to pull slurry through the filter.

The filtrate chamber includes a filtrate drain to pass the filtrate into the measurement cell. The measurement cell is coupled to a light source so that light propagating from the light source is attenuated by the liquid mixture in the measurement cell, and is measured by an optical detector that is also coupled to the measurement cell. The optical detector generates an attenuation spectrum indicating light received by the detector at different wavelengths. The attenuation spectrum is used to determine characteristics of the soil sample. In some embodiments, additional measurement devices are coupled to the filtration system to perform additional measurements of the characteristics of the soil sample.

Embodiments of the filtration system may also enable cleaning of the chambers and filter. A cleaner inlet coupled to the filtrate chamber introduces a volume of cleaning fluid into the filtrate chamber. To pressure clean the filter, the filtrate chamber receives a volume of cleaning fluid sufficient to cover the perforations of the filter. An air source pressurizes the filtrate chamber which causes the filtration system to force the cleaning fluid backwards (in a direction opposite of filtration) from the filtrate chamber through the filter into the slurry chamber. The backwards flow of cleaning fluid may dislodge particulate stuck in the filter. Cleaning fluid may also be introduced into the slurry chamber and passed through the filter in a process similar to that for generating filtrate. The air source coupled to one or both of the chambers may be used to pass air through the chambers and measurement cell to dry the filtration system. The air drying my also occur in the forwards and backwards directions to ensure the filtration system is fully dried in preparation for another measurement.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

STRUCTURE OF SOIL ANALYSIS DEVICE

Overview

Figure 1:
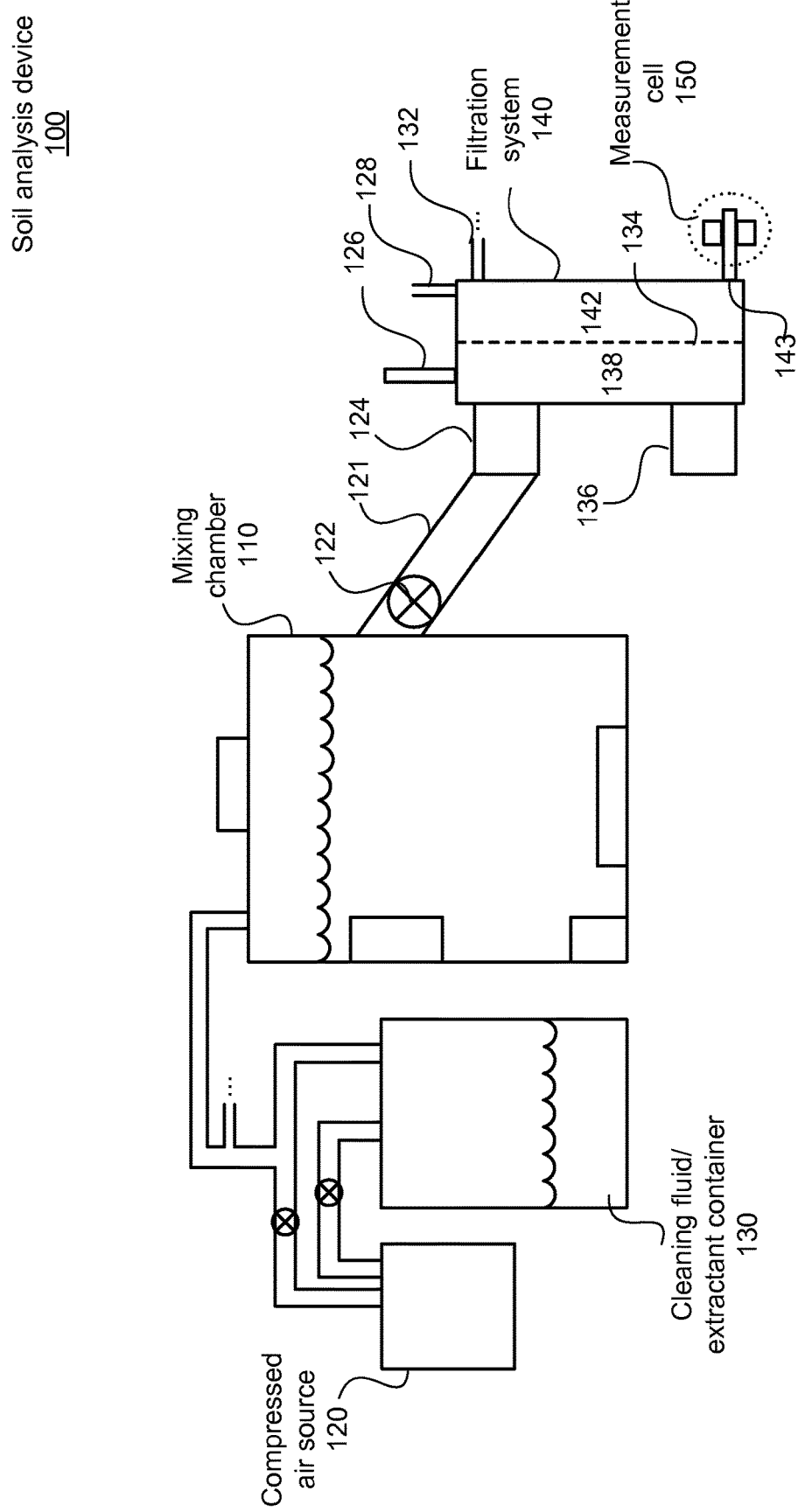
FIG. 1 is a soil analysis device configured to create soil sample solutions and to self-clean between soil samples, according to one embodiment.

FIG. 1 is a block diagram of one embodiment of a soil analysis device 100. In one embodiment, the soil analysis device 100 includes a mixing chamber 110, a compressed air source 120, one or more cleaning fluid and/or extractant containers 130, a filtration system 140 and a measurement cell 150. In an alternative embodiment, the measurement cell 150 is absent and the device 100 comprises an output port (not shown) for apportioning out a filtered volume of solution for collection and testing external to the device 100. The soil analysis device 100 also includes a control system (not shown) for controlling the operation of the soil analysis device.

Generally, the mixing chamber 110 is configured to receive a field moist soil sample and extractant, mix them together, and provide the mixed solution (or slurry) to the filtration system 140. The filtration system 140 filters the slurry and provides the filtered output either to the measurement cell 150 for testing, or to the output port (not shown). In one embodiment, the unfiltered slurry that is not filtered by the filtration system 140 may also be supplied as a separate output. The soil analysis device 100 is further configured to use air from the compressed air source 120 and a cleaning fluid from a container 130 to automate self-cleaning of the mixing chamber 110, filtration system 140, and/or the measurement cell 150 or output port. Automated self-cleaning cleans the various components of the device 100 so that the measurement of later received soil samples is not tainted by previously received soil samples.

The filtration system 140 filters the slurry to remove unwanted particulate. Specifically, the filtration system 140 is configured to remove particulate that would otherwise interfere with the optical measurement of the slurry by measurement cell 150. A benefit of filtering the slurry is that comparatively less dilution of the original soil sample by extractant is needed to achieve the same optical clarity if the slurry is filtered than if it is not. Less dilution of the soil sample improves the signal to noise ratio of optical measurements performed by measurement cell 150. Thus, filtering the slurry prior to measurement improves quality of the measurements made.

The measurement cell 150 includes a light source so that light propagating from the light source is attenuated by filtrate in the measurement cell 150, and is measured by one or more optical detectors that are coupled to the measurement cell. The optical detectors generate an attenuation and/or a reflection spectrum indicating light received by the detectors at different wavelengths. The attenuation and/or reflection spectrums are used to determine characteristics of the field moist soil sample.

Filtration System

The filtration system 140 will now be described in more detail. The filtration system 140 includes a slurry inlet 124 coupled to a pipe 121 for receiving the slurry from the mixing chamber 110. The pipe 121 is configured with a slurry inlet valve 122 to control flow of the slurry into the filtration system 140. The slurry inlet valve 122 may be opened or closed in either a manual or automated fashion. In one embodiment, the slurry inlet valve 122 is a pinch valve. Pinch valves are advantageous due to the soil component of the liquid mixture. The soil portions of the liquid mixtures may, through repeated use, clog valves, hindering their opening and closing motion thereby affecting the ability to control the amount of liquid mixture that is transferred through pipe 121. Pinch valves are less prone to clogging due to dirt than some other types of valves. In another embodiment, the slurry inlet valve 122 is a seated valve. Seated valves include a compliant stopper driven by an actuator, such as a piston. The actuator drives the compliant stopper against a seat to seal an opening of the valve 122 when the valve is closed. In turn, the actuator pulls the compliant stopper away from the seat to allow liquid or slurry to flow freely through the opening of the valve when the valve is opened. Seated valves are advantageous as the stopper and seat can be designed such that there exists a wide clearance in the open position, reducing the likelihood of clogs in the valve. In one embodiment, the opening is around half an inch in diameter.

The slurry chamber 138 is separated from a filtrate chamber 142 by a filter 134. The filter 134 removes unwanted particulate from slurry passing through it to generate filtrate in the filtrate chamber 142. The size of particulate filtered from the slurry may be adjusted based on the porosity of the filter 134. For example, the pore sizes in the filter may be set between 1-10 micrometers. In one embodiment, the filter 134 is constructed of a material capable of reuse. For example, the filter 134 may be constructed from a porous metal sheet. As a specific example, the filter 134 may be made of sintered, porous 316L stainless steel with an average pore size between 1 and 5 micrometers and approximate thickness between 0.05 and 0.15 inches.

After the slurry chamber 138 is filled such that the porous filter 134 surface is covered by slurry, the slurry inlet valve 122 controlling flow of slurry through the inlet 124 may be closed. As a result of slurry passing through the filter 134 from the slurry chamber 138 into the filtrate chamber 142, fine particulates may be left embedded in the filter surface. This can have the effect of improving the efficiency of the filtration process beyond what would otherwise be possible for a given average filter pore size.

Alternatively to using a reusable filter, the filter 134 may instead be a disposable filter (e.g., one time use), such as filter paper. The filter paper may be, for example, a specially designed filter paper cut to fit a frame of the filter 134.

Filtered slurry that has passed through the filter 134 (also referred to as filtrate) collects in the filtrate chamber 142. The filtrate chamber 142 includes a filtrate drain 143 for feeding the measurement cell 150 or otherwise collecting filtrate. The measurement cell 150 may include its own separate drain, such that filtrate may flow from the filtrate chamber 142, through the measurement cell 150 and subsequently flow out of the device 100. The filtrate drain 143 may include a valve (not shown) for controlling the flow of filtrate into the measurement cell 150. For example, the valve may be adjusted to provide the analysis device 100 with the ability to measure soil nutrient concentrations (e.g., nitrate or nitrate-nitrogen) in the filtrate continuously, as well as monitor when the filtration system 140 has run out of filtrate to measure. The valve may remain closed until a certain amount of time has passed or a given volume of filtrate is collected in the filtrate chamber 142 to prevent passage of air with filtrate into the measurement cell 150. Additionally, the valve may be adjusted to drain a portion of initial filtrate from the filtrate chamber 142 to prevent dirtier, early filtrate from clouding and contaminating later, cleaner samples passing through the measurement cell 150.

The filtration system 140 may filter the slurry under pressure to increase the speed of filtration and reliability of producing repeatable samples of the slurry for measurement in the measurement cell 150. The slurry is introduced to the slurry chamber 138 and impeded from flowing into the filtrate chamber 142 by the filter 134. In order to increase the speed at which filtrate is collected in the filtrate chamber 142, the slurry chamber 138 may be pressurized by a compressed air source 120 to force the slurry against (and through) the filter 134. For example, the slurry chamber 138 may include a pressurization valve 126 coupled via a pipe to the compressed air source 120. In some embodiments, the pressurization valve 126 may also include a pressure release to vent the slurry chamber 138 to atmosphere. Allowing the slurry chamber 138 to vent to atmosphere as slurry is introduced into the chamber may increase flow rate of the slurry (i.e., by preventing backflow of air into the mixing chamber), thus enabling the slurry chamber 138 to fill more quickly to reduce measurement time. The vent remains closed when the pressurization valve 126 is opened to pressurize the slurry chamber 138 or the slurry chamber 138 is otherwise pressurized (e.g., in instances where slurry is pressurized at the mixing chamber).

When the pressurization valve 126 is opened, the slurry in the slurry chamber 138 is pressurized by the compressed air source 120, forcing the slurry through the filter 134 to generate the filtrate at a greater rate than otherwise possible. In this example, in addition to controlling the flow of the slurry, the slurry inlet valve 122 may be substantially airtight when closed or otherwise prevent backflow of slurry and/or air into the mixing chamber 110 when the filtration system 140 is pressurized. In other embodiments, the slurry in the mixing chamber 110 is pressurized by the compressed air source 120 to force slurry into the slurry chamber 138 via inlet 124 and through the filter 134.

In some embodiments, the compressed air source 120 may be used to generate a vacuum in the filtrate chamber 142. The vacuum may be used for evacuating trapped air from the filter assembly to aid in allowing the slurry chamber 138 to fill quickly and/or helping to pull the slurry through the filter 134. For example, the filtrate chamber 142 may include a vacuum valve 128 coupled via a pipe to a compressor (not shown) of the compressed air source 120. Activating the compressor and opening the vacuum valve 128 creates a vacuum in the filtrate chamber 142, thereby pulling slurry through the filter 134 in the filtrate chamber 142. In one embodiment, the vacuum valve 128 is opened, with or without additional pressurization applied to the slurry chamber 138, to quickly generate an initial amount of filtrate in the filtrate chamber 142 prior to passing filtrate through the filtrate drain 143. The vacuum valve 128 may also include a pressure release to vent the filtrate chamber 142 to atmosphere. Venting the filtrate chamber 142 to atmosphere can prevent backflow (i.e., the introduction of air bubbles to the filtrate) from the measurement cell 150 when the filtrate drain 143 valve is opened.

The slurry chamber 138 may also include a slurry outlet 136 allowing removal of the contents of the slurry chamber 138 in preparation for a cleaning process and subsequent sample. The slurry outlet 136 may include a valve (not shown) that may be opened or closed in either a manual or automated fashion to allow drainage of the contents of the slurry chamber 138, for example, after filtered slurry has been measured in the measurement cell 150. In one embodiment, the outlet 136 may be an opening having a movable cover (not shown), so that moving the cover allows the contents of the slurry chamber 138 to drain. In either instance, closing the valve or cover of the slurry outlet 136 prevents drainage of the slurry from the slurry chamber 138 during filtration.

In some embodiments, the filtration system 140 is configured to enable a self-cleaning of the chambers 138, 142, filter 134 and measurement cell 150. The cleaning process may be automated or performed manually. As shown, filtrate chamber 138 includes a cleaner inlet 132 for receiving a cleaning fluid, such as water, in the filtrate chamber 142. The cleaner inlet 132 is coupled to one of the containers 130 via a pipe (not shown). Alternatively, or in addition to receiving cleaning fluid via the inlet 132, cleaning fluid may be received in the slurry chamber 138 from the mixing chamber through pipe 121. In this case, cleaning fluid is passed from container 130, through the device 100, and into chamber 138 when no slurry is present in the device 100. In some embodiments, the filtration system 140 utilizes the backwards flow of cleaning fluid through the filter 134 to remove embedded particulate in filter media during the cleaning process. The slurry outlet 136 may be opened to drain cleaning fluids and excess slurry particulate from the filtration system 140. In turn, the filtrate drain 143 may be opened to drain any cleaning fluid and filtrate. Passing cleaning fluid in this manner helps dislodge particulate stuck in the filter 134 during slurry filtration, and helps flush excess slurry and filtrate present in the chambers 138, 142 after a measurement has been conducted.

In a specific example, cleaning fluid introduced into the filtrate chamber 138 may be passed backward through the filter 134 from chamber 138 to chamber 142 and flushed from the slurry chamber 138 through opening the slurry outlet 136. The slurry outlet 136 may, in turn, close to allow cleaning fluid introduced via the inlet 132 to collect in the slurry chamber 138. The cleaning fluid in the slurry chamber 138 may be passed forwards through the filter 134 from chamber 142 to chamber 138 and flushed from the filtrate chamber 142 through the measurement cell 150. Passing cleaning fluid both forward and backward through the filtration system in this manner may improve the amount of left-over material removed from the filtration system 140.

The filtration system 140 may also pressurize (or form a vacuum in) the chambers 138, 142 as needed to more forcefully pass cleaning fluid through the filter 134 in the backward and/or forward directions. For example, the filtration system 140 may pressurize (e.g., via valve 128) the filtrate chamber 142 using a compressor of the compressed air source 120 to help pass cleaning fluid through the filter 134 into the slurry chamber 138. In turn, the slurry drain 136 may be opened to flush the cleaning fluid. Alternatively, or in addition to pressurizing the filtrate chamber 142, the filtration system 140 may form a vacuum (e.g., via valve 126) the slurry chamber 138 using the compressed air source 120 to help pull cleaning fluid through the filter 134 and into the slurry chamber 138. The opposite steps may be taken to help clean the filter 134 in the forward direction and the filtrate drain 143 opened to flush the cleaning fluid. Alternatively, the cleaning fluid in the filtrate chamber 142 may be passed back through the filter 134 into the slurry chamber 138 to drain.

The compressed air source 120 may also be used to dry the chambers 138, 142, filter 134 and measurement cell 150. Similar to the flow of cleaning fluid through the filtration system 140, air may be passed in a forwards and backwards direction through the filter 134. To pass air in a given direction (e.g., forward) through the filter 134, one chamber (e.g., 138) is pressurized and an outlet (e.g., filtrate drain 143) of the other chamber is opened. Subsequently forming a vacuum in the same chamber 138 or pressurizing the other chamber 142 and opening the slurry outlet 136 may be used to pass air in the other direction. These steps eliminate any leftover soil sample and cleaning fluid from the filtration device 140 in preparation to receive a new sample.

Example Filtration System

Figure 2A:
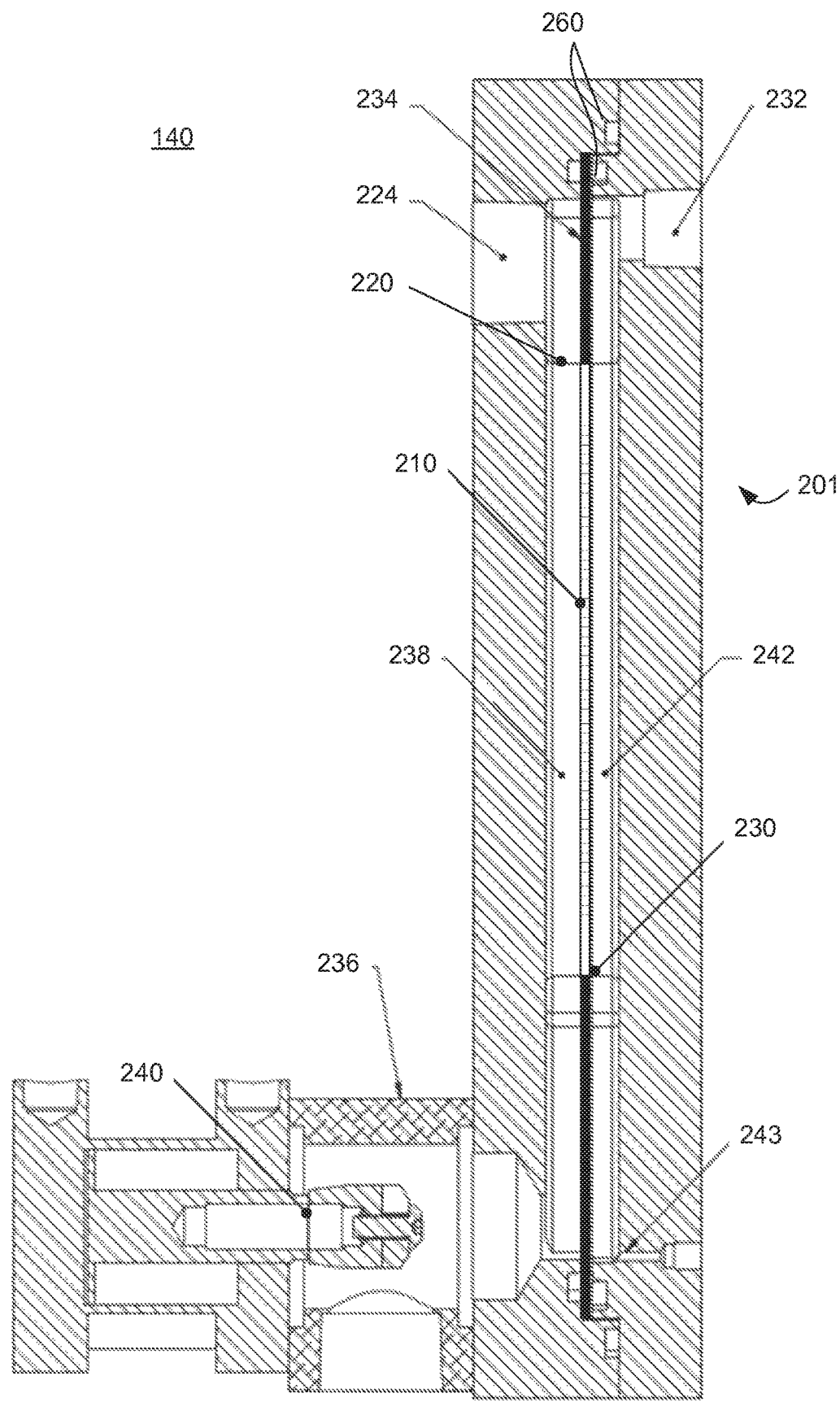
FIG. 2A is a side view of a filtration system for filtering a soil sample solution, according to one embodiment.

FIG. 2A is a side view of a filtration system 140 for filtering a soil sample solution, according to one embodiment. As shown, the filtration system 140 includes a filter 234 partitioning a slurry chamber 238 and a filtrate chamber 242. Additionally, as described with reference to FIG. 1, the slurry chamber 238 and/or filtrate chamber 242 may include valves (not shown for clarity) coupled to a compressed air source 120 for pressurizing and/or vacuuming the chambers during filtration and cleaning. In the depicted embodiment, the filtration system 140 is oriented vertically, with ground being located parallel with the bottom of the figure. Consequently, gravity acts as a downward force along the vertical axis of the depicted figure. In other embodiments, the filtration system 140 may be oriented in other directions and will still function similarly.

The slurry chamber 238 is coupled to a slurry inlet 224 at its top and a slurry drain 236 at its bottom. The size of the slurry inlet 224 and drain 236 may be configured as desired to a diameter sufficient to allow the slurry to flow into and out of the chamber, preferably without clogging. The assembly of the slurry drain 236 may include a valve 240 that is actuated manually, or automatically, to open and seal the drain 236. The slurry chamber 138 may also include a vent valve (not shown) for venting the chamber 138 to atmosphere, allowing trapped air in the chamber to escape while filling the chamber.

The filtrate chamber 242 is coupled to a cleaner inlet 232 at its top and a filtrate drain 243 at its bottom. The filtrate drain 243 may include an assembly (not shown) with a valve (e.g., of different scale, but functionally similar to that of valve 240) to control the flow of filtrate collected in the filtrate chamber 242 to a measurement cell (not shown). The filtrate drain 243 may be a smaller size than the slurry drain 236 as the filter 234 removes clogging particulate and to better control the flow of filtrate into the measurement cell.

For scale, in one embodiment, the filtration system 140 is about 0.5-4 inches in depth and 9-21 inches tall and about 3-7 inches wide to provide a large, vertical filter 234 surface area. In one embodiment, the height-width ratio is approximately 3:1. The filter 234 itself may be approximately the same dimensions, with the perforations/perforated area configured as described below. The filter 234 may also be larger or smaller. The filter 234 may be sandwiched between a front plate forming the filtrate chamber 242 and a black plate forming the slurry chamber 238 which are all held together using a number of fasteners 260. Compressible seals (not shown) such as a gasket or o-ring may run the length of the junctions between the surfaces of the filter 234, the back plate forming the slurry chamber 238, and/or the front plate forming filtrate chamber 242 to prevent air/slurry leakage between the chambers and filter. In an alternate embodiment, the front plate and back plate may be constructed as a single piece (or affixed) with a slit at the top for the filter 234 to slide into to form the slurry and filtrate chambers.

As described previously, embodiments of the filter 234 may include a number of perforations 210 (not shown to scale) that allow slurry to pass through the filter 234. The perforations cover at a portion of the surface area of the filter 234 up to a slurry line 220. The slurry fill line 220 indicates the volume of slurry in the slurry chamber 238 that covers the perforations 210. If the slurry chamber 238 is filled to this line, the slurry chamber can be pressurized and/or a vacuum formed in the filtrate chamber 242 to assist with filtrate creation. Similarly, if filled with cleaning fluid at or above this line 220 in a given chamber 238 or 242, the given chamber can be can be pressurized and/or the other have a vacuum formed therein to help clean the filter 234 during a cleaning sequence. Once the slurry volume falls below the fill line 220, air will flow from the slurry chamber 238 to the filtrate chamber 242 through the filter 234 perforations 210, thus equalizing the pressure.

In a specific embodiment, the perforations 210 may extend the width of the filter and vertically from a filtrate fill line 230 to a slurry fill line 220. As larger particulate typically collects at the bottom of the slurry chamber 238, the portion of the filter 234 below the filtrate fill line 230 may not include any perforations as its contribution to filtrate generation may be minimal. Additionally, provided the volume of filtrate in the filtrate chamber 242 at the filtrate fill line 230 is sufficient for providing a measurement reading, the slurry drain valve 240 may be opened to begin draining the slurry chamber 238.

Other embodiments may includes filters 234 where the perforations 210 extend from the slurry fill line 220 to the bottom of chambers 238 and 242. Additionally, in embodiments where cleaning fluid and slurry are pressurized in the container 130 and mixing chamber 110, respectively, the perforations may extend to the top of the filter 134 rather than the slurry fill line 220.

By orienting the filter surface vertically, cleaning and drying of the filter 234 is made easier, however alternate embodiments may have the filter in a horizontal orientation, which may reduce the tendency for the filtrate to contain bubbles. Other implementations used cylindrical filters with the slurry chamber formed on the inside of the cylinder and the filtrate chamber on the outside or vice versa. One skilled in the art will recognize the configuration of the inlets 224, 232, drains 236, 243, and filter 234 may deviate from the embodiment shown in FIG. 2A to accommodate these alternate embodiments.

A table 1 illustrating example combinations for passing filtrate, cleaning fluid, and/or air through the filter and filtration system are shown for reference:

TABLE 1

| Chamber | Fluid | Pressure | Vacuum | Inlets/Outlets | Result |
|---|---|---|---|---|---|
| Slurry 238 | Slurry in chamber 238 | Y | N | Drain 236 Closed | Generate Filtrate |
| Filtrate 242 | Slurry in chamber 238 | N | Y | Drain 243 Closed | Generate Filtrate |
| Filtrate 242 | Slurry in chamber 238 | N | N | Drain 243 Open | Pass Filtrate to Cell 150 |
| Slurry 238 | Cleaner in chamber 238 | Y | N | Drain 236 Closed, Drain 243 Open | Pass Cleaner Forward & Drain |
| Slurry 238 | Cleaner in chamber 242 | N | Y | Drain 236 Closed | Pass Cleaning Fluid Backward |
| Filtrate 242 | Cleaner in chamber 238 | N | Y | Drain 243 Closed | Pass Cleaning Fluid Forward |
| Filtrate 242 | Cleaner in chamber 242 | Y | N | Drain 243 Closed, Drain 236 Open | Pass Cleaner Backward & Drain |
| Slurry 238 | Air | Y | N | Drain 236 Closed, Drain 243 Open | Pass Air Forward |
| Slurry 238 | Air | N | Y | Drain 236 Closed, Drain 243 Open | Pass Air Backward |
| Filtrate 242 | Air | Y | N | Drain 243 Closed, Drain 236 Open | Pass Air Backward |
| Filtrate 242 | Air | N | Y | Drain 243 Closed, Drain 236 Open | Pass Air Forward |

Some embodiments may utilize more than one combination at once, for example, the slurry chamber 238 may be pressurized and the filtrate chamber 242 under vacuum at the same time and vice versa. Additionally, the use of pressurization and/or vacuum during any given step for generating filtrate or passing of cleaning fluid may be optional, for example, if a sample is gravity filtered or the system does not include a vacuum. Some combinations may include operation of additional or less hardware depending on the embodiment.

Figure 2B:
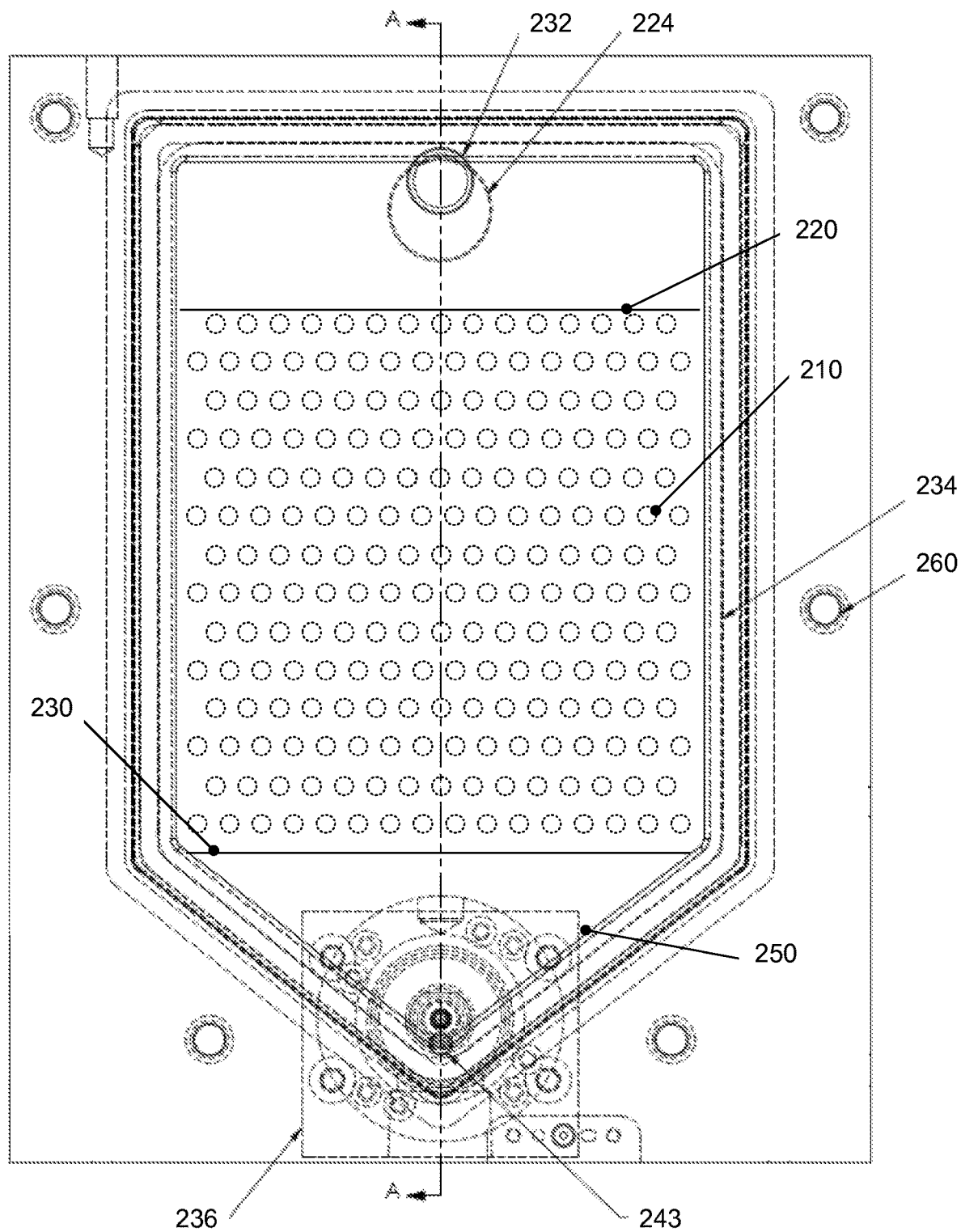
FIG. 2B is a front view of a filtration system for filtering a soil sample solution, according to one embodiment.

FIG. 2B is a front view 201 of a filtration system 140 corresponding to the example embodiment illustrated in FIG. 2A for filtering a soil sample solution, according to one embodiment. The side view cut A, illustrated in FIG. 2A, is shown for reference.

The perforations 210 of the filter 234 extend across the width of the filter and vertically from the slurry fill line 220 to the filtrate fill line 230. The bottom portion of the chambers may be formed as a trough 250 for guiding the filtrate/slurry to the bottom of the respective chambers and out the filtrate drain 243 and slurry drain 236.

Slurry Filtration

Figure 3:
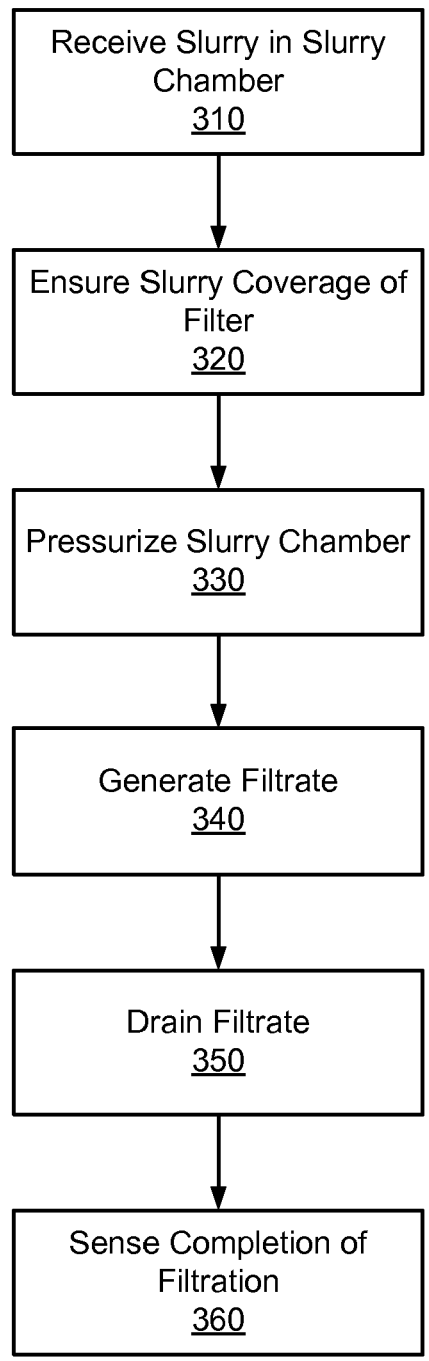
FIG. 3 is a flow chart of one embodiment of a method for generating filtrate from slurry using the filtration system in the soil analysis device.

FIG. 3 is a flow chart of one embodiment of a method 300 for generating filtrate from slurry using the filtration system 140 in the soil analysis device 100. In the embodiment shown by FIG. 3, the slurry chamber 138 receives a liquid mixture (or slurry) comprising a portion of a soil sample mixed with an extractant such as water and optionally a salt.

The slurry inlet valve 122 remains open for at least a first duration sufficient to ensure 320 slurry coverage of the filter 134. The slurry inlet valve 122 may also remain open for a further second duration sufficient to introduce an additional volume of slurry into the slurry chamber 138 after some slurry has already filtered through the filter 134 in order to generate enough filtrate to perform a measurement.

Once enough slurry is collected in the slurry chamber 138, the inlet valve 122 may be closed to seal the chamber in instances where the slurry chamber 138 is pressurized 330 through opening of the slurry pressurization valve 126 at the top of the chamber. In alternate embodiments where the slurry itself introduced into the chamber 138 under pressure (e.g., when the slurry is pressurized in the mixing chamber), the inlet valve 122 may remain open until filtration concludes. In either instance, the slurry chamber 138 is pressurized by way of the slurry in the chamber covering the filter to create a pressure differential between the chambers (across the filter) to accelerate the generation 340 of filtrate in the filtrate chamber 142.

In some embodiments, the filtrate chamber 142 includes a vacuum valve 128 for generating a vacuum in the filtrate chamber 142 to pull air out of the filter chamber to aid in filling the slurry chamber 138 and/or to help pull slurry through the filter 134 during pressure filtration at a greater rate than otherwise possible. The vacuum valve 128 may be used for a given duration in a pre-measurement stage to quickly generate 340 an initial volume of filtrate prior to filtrate being allowed to enter a measurement cell 150. In order to prevent backflow from the measurement cell 150, the filtrate drain 143 remains closed while the vacuum valve 128 is open and/or a vacuum persists in the filtrate chamber 143. After the duration of the pre-measurement stage, the vacuum valve 128 vents the filtrate chamber 142 (e.g., to atmosphere) prior to opening of the filtrate drain 143.

The filtrate drain 143 is opened to drain 350 filtrate collected in the filtrate chamber through the measurement cell 150. The filtrate drain 143 may regulate the flow of filtrate to ensure that enough filtrate flows through the measurement cell 150 throughout a reading period without depleting the volume of filtrate collected in the filtrate chamber 142. Depleting the filtrate chamber 142 may introduce unwanted gases into the measurement cell 150 and provide an inaccurate reading.

The measurement cell 150 may sense 360 completion of filtration through the detection of gasses in the filtrate. Specifically, the measurement cell 150 may halt filtration based on the measured absorbance spectra of filtrate including a significant proportion of air rather than sample. Alternatively, the measurement cell 150 may sense 360 completion of a measurement (e.g., due to a stable reading) of the filtrate prior to detection of the change in absorbance spectra due to the presence of air (e.g., prior to generating the entire volume of filtrate). In either instance, the slurry drain 136 and/or filtrate drain 143 may be opened to pass excess slurry/filtrate from the filtration system 140. Optionally, the pressurization valve 126 may be closed at this stage. In an alternative embodiment, filtration may be stopped after a particular period of time or responsive to a user input to cease filtration.

In some embodiments, the entire volume of filtrate may be generated 340 prior to a measurement or for collection in a vessel for a later measurement. In turn, the vacuum valve 128, in addition to the pressurization valve 126, may remain open to create the vacuum until the desired volume of filtrate is generated in the filtrate chamber 142. For this example, sensing 360 of the completion of filtration may occur prior to venting of the filtrate chamber 142 and subsequent opening of the filtrate drain 143 to drain 350 filtrate to prevent backflow from the vessel or measurement cell. Additionally, depending on the embodiment of the filtration system 140, opening of the slurry drain 136 may have to wait until the collected filtrate is drained from the filtrate chamber 142.

Filtration System Cleaning Cycle

Figure 4:
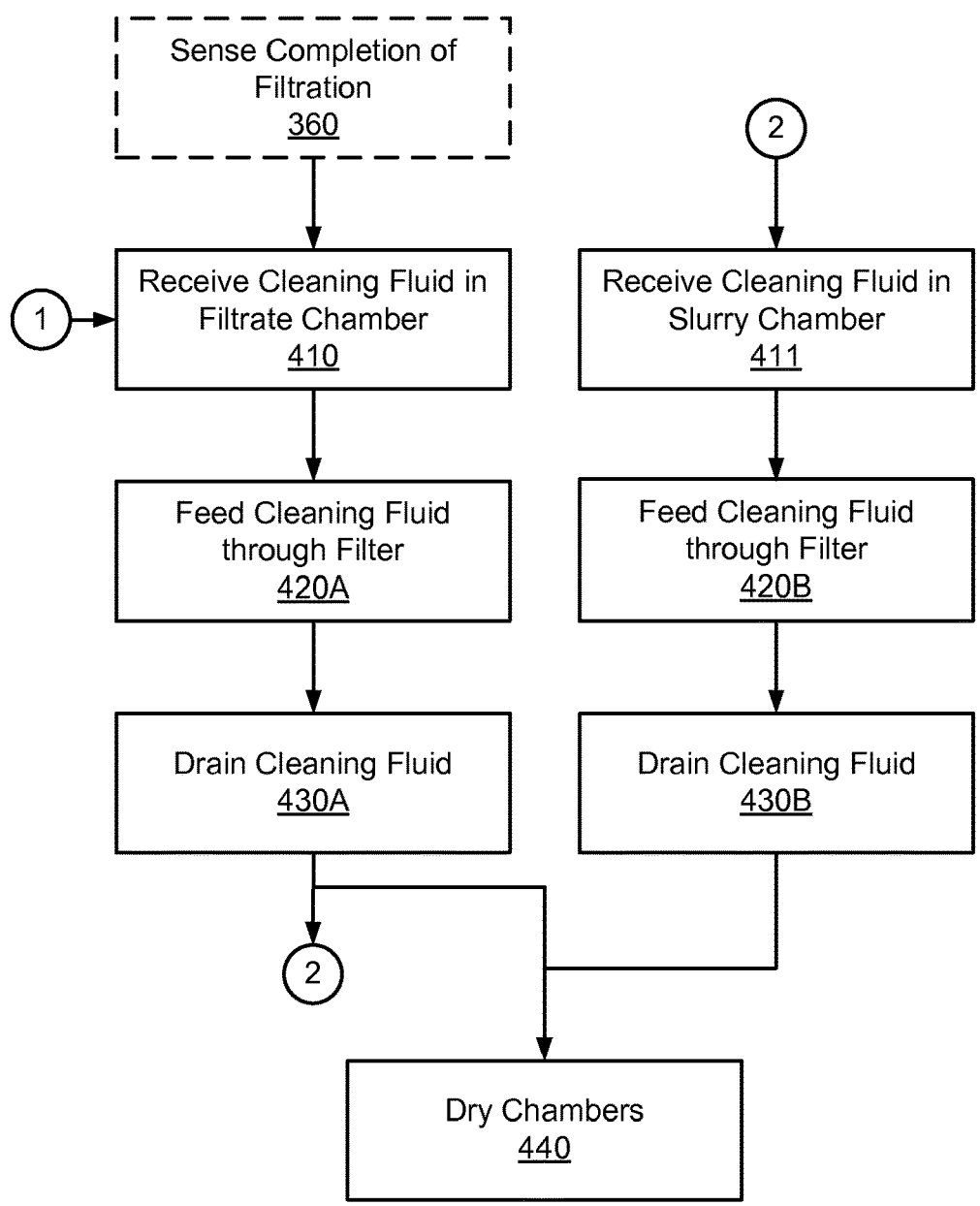
FIG. 4 is a flow chart of one embodiment of a method for cleaning the filtration system in the soil analysis device.

FIG. 4 is a flow chart of one embodiment of a method 400 for cleaning the filtration system 140 in the soil analysis device 100. In the embodiment shown by FIG. 4, the cleaning cycle 400 may optionally be initiated once completion of filtration 360 is sensed or alternatively, prior to performing a measurement.

Prior to cleaning or as an initial step in the cleaning process, the slurry drain 136 and filtrate drain 143 may be opened to drain any slurry/filtrate in the chambers 138, 142 of the filtration system 140. Additionally, a drain of the measurement cell 150 may be opened to pass excess filtrate received from the filtrate chamber 142 through the cell.

To clean a backward direction through the filter 134 (starting at the circle labeled as 1 in FIG. 4), the filtration system 140 receives 410 a cleaning fluid, such as water, in the filtrate chamber 142 through the cleaner inlet 132. The filtrate drain 143 may be closed in order to more easily fill the filtrate chamber 142 to the top of the filter 134. In contrast, the slurry drain 136 is opened to drain any cleaning fluid passed through the filter 134 from the filtrate chamber 142.

Accordingly, the filter system 140 feeds 420A the cleaning fluid through the filter 134 from the filtrate chamber 142 to the slurry chamber 138. Ideally, the feeding 420A of cleaning fluid in this direction (i.e., backwards through the filter) dislodges particulate caught in the filter 134 such that it flows out the slurry drain 136. After a desired duration of cleaning, the filtration system 140 stops the influx 410 of cleaning fluid in the filtrate chamber 142 and allows the slurry chamber 138 to drain 430A the cleaning fluid and dislodged particulate.

In some embodiments, the chambers 138, 142 may be vacuumed and/or pressurized during the backwards cleaning phase (1) to pass cleaning fluid through the filter 134 with greater force to dislodge particulate. In the case of creating a vacuum in the slurry chamber 138, in one embodiment, the slurry drain 136 and slurry inlet 124 remain closed and a valve coupled to a compressor of the compressed air source 120 is opened. In the case of pressurizing the filtrate chamber 142, cleaning fluid under pressure is received from container 130 via inlet 132 or the chamber 142 is pressurized via a valve coupled to the compressed air source 120. In either case, the filtration system 140 receives sufficient cleaning fluid to ensure that the cleaning fluid covers the filter 134.

To clean in a forward direction through the filter 134 (starting at the circle labeled as 2 in FIG. 4), the filtration system 140 receives 411 a cleaning fluid in the slurry chamber 132 through the slurry inlet 124. The slurry drain 136 may be closed in order to more easily fill the slurry chamber 138 to the top of the filter 134. In contrast, the filtrate drain 143 is opened to drain any cleaning fluid passed through the filter 134 from the slurry chamber.

Accordingly, the filter system 140 feeds 420B the cleaning fluid through the filter 134 from the slurry chamber 138 to the filtrate chamber 142. After a desired duration of cleaning, the filtration system 140 stops the influx 411 of cleaning fluid in the slurry chamber 138 and allows the filtrate chamber 142 to drain 430B the cleaning fluid.

In some embodiments, the chambers 138, 142 may be pressurized and/or vacuumed during the reverse cleaning phase (2) to pass cleaning fluid through the filter 134 with greater force. In the case of creating a vacuum in the filtrate chamber 138, in one embodiment, the cleaner inlet 132 and filtrate drain 142 remain closed and the vacuum valve 128 is opened. In the case of pressurizing the slurry chamber 138, cleaning fluid under pressure is received from the mixing chamber 110 via inlet 124 or the chamber 142 is pressurized via pressurization valve 126. In either case, the filtration system 140 ensures that the cleaning fluid covers the filter 134. As described above, the filter 134 may be cleaned in both the forward and reverse directions in order to remove as much particulate as possible from the filter 134. Although described above as cleaning in the forward direction followed by cleaning in the reverse direction, the order of these operations may be reversed in another embodiment.

Subsequently to both forward and reverse cleaning with a cleaning fluid, the filter system 140 is air dried to remove any leftover cleaning fluid as well as to ideally flush any remaining particulate. At this stage, both drains 136, 143 are opened and the chambers are allowed to dry 440. Pressurized air from compressed air source 120 may also be blown into one or more of the chambers 138, 142 to hasten the drying process. As with the reverse (1) and forward (2) cleaning fluid process described above, pressurized air cleaning may also be performed in a forward and reverse manner, in either order. This may be accomplished, for example, by opening and closing the valves, inlets, and outlets of the filtration system 140 in a similar manner as described above.

Soil Analysis Device Operation

Figure 5:
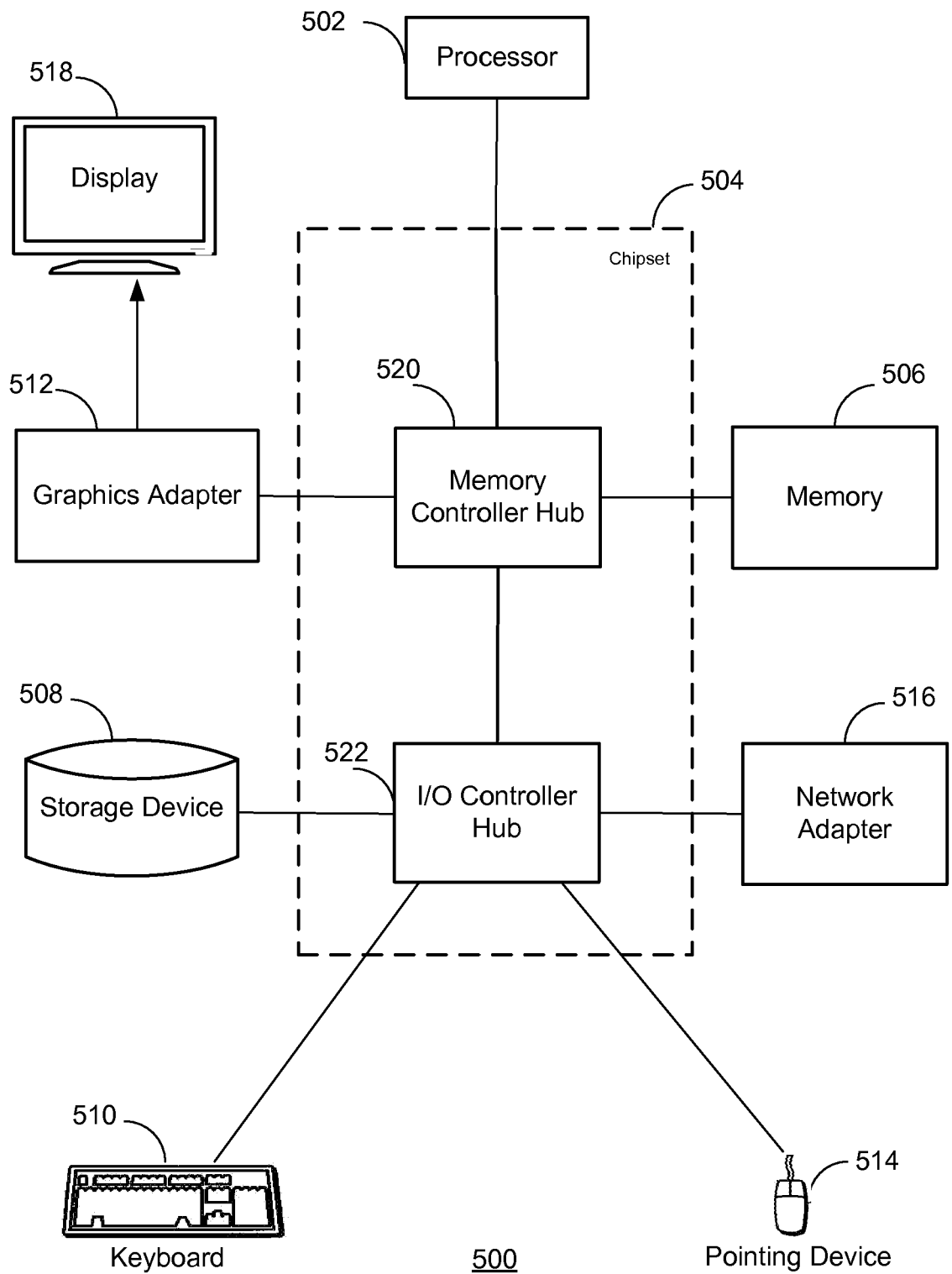
FIG. 5 is a high-level block diagram illustrating an example of a computer for controlling a soil analysis device, according to one embodiment.

FIG. 5 is a high-level block diagram illustrating an example of a computer 500 for use in controlling the operation of the soil analysis device 100, according to one embodiment. For example, the computer control system 500 may be used to control the opening and closings of the various valves, lids, and chambers of the filtration system 140, control the compressed air source 120 and compressor, and thereby control the motion of soil samples, filtrate, air, and cleaning fluid through the soil analysis 100 device in general, and through the filtration system 140 particularly.

Illustrated are at least one processor 502 coupled to a chipset 504. The chipset 504 includes a memory controller hub 520 and an input/output (I/O) controller hub 522. A memory 506 and a graphics adapter 512 are coupled to the memory controller hub 520, and a display device 518 is coupled to the graphics adapter 512. A storage device 508, keyboard 510, pointing device 514, and network adapter 516 are coupled to the I/O controller hub 522. A code scanner (e.g., a barcode scanner or RFID scanner, not shown) can also be coupled to the I/O controller hub 522. Other embodiments of the computer 500 have different architectures. For example, the memory 506 is directly coupled to the processor 502 in some embodiments.

The storage device 508 includes one or more non-transitory computer-readable storage media such as a hard drive, compact disk read-only memory (CD-ROM), DVD, or a solid-state memory device. The memory 506 holds instructions and data used by the processor 502. The pointing device 514 is used in combination with the keyboard 510 to input data into the computer system 500. The code scanner (not shown) is used to input data into the computer system 500. The graphics adapter 512 displays images and other information on the display device 518. In some embodiments, the display device 518 includes a touch screen capability for receiving user input and selections. The network adapter 516 couples the computer system 500 to an external network (e.g., a local area network, a wireless network, or the internet). Some embodiments of the computer 500 have different and/or other components than those shown in FIG. 5.

The computer 500 is adapted to execute computer program instructions for controlling the operation of the soil analysis 100. Instructions can be implemented in hardware, firmware, and/or software. In one embodiment, executable computer program instructions are stored on the storage device 508, loaded into the memory 506, and executed by the processor 502.

Measurement Cell

Figure 6:
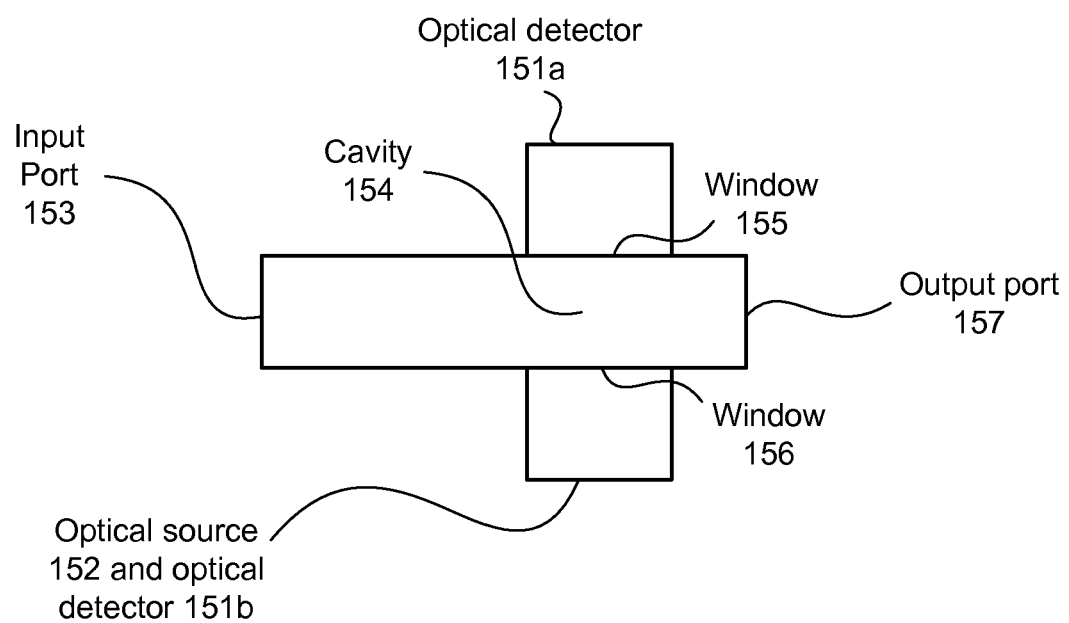
FIG. 6 is a block diagram of a measurement cell for analyzing a soil sample solution, according to one embodiment.

FIG. 6 is a block diagram of a measurement cell for analyzing a soil sample solution, according to one embodiment. The measurement cell 150 is configured to optically measure characteristics of the soil sample solution received from the filtration system 140. The measurement cell 150 includes or is coupled to an input port 153 for receiving the soil sample solution, a cavity 154, one or more windows 155, 156, an optical source 152, one or more optical detectors 151a, 151b, and an output port 157.

The optical source 152 initiates the measurement of the characteristics of the soil sample solution by passing light through the received soil sample solution. A detector 151a is placed opposite from the optical source 152 across the cavity 154, to capture an attenuation spectrum of the light passing through the soil sample solution as a function of wavelength. In one embodiment, detectors 151 are spectrometers having a 1 to 4 nanometer resolution. The detectors 151 have a sufficient sensitivity to allow detection of light passing through materials having a high absorbance. This allows the detectors 151 to determine an attenuation spectrum associated with a soil sample solution by determining how different wavelengths of light are attenuated by the soil sample solution present in the cavity 154.

In one embodiment, a second detector 151b is placed on the same side of the cavity 154 as the light source 152, in order to obtain a reflection spectrum of the light reflected from the soil sample solution. The reflection spectrum may be used to determine characteristics of the soil sample.

Peaks in the attenuation spectrum allow identification of components of the soil. For example, attenuation peaks at wavelengths of approximately 200 nanometers and 300 nanometers indicate nitrate-nitrogen in the soil. Similarly, attenuation peaks at wavelengths of approximately 210 nanometers, 230 nanometers and 250-300 nanometers may be used to identify nitrite-nitrogen, bisulfide and organic carbon, respectively, in the soil. Other peaks in the attenuation spectrum may also be used to identify additional components of the soil. Additionally, if the soil sample solution contains chemicals in addition to soil and extractant, additional attributes of the soil in a sample may be determined from the effect of the chemicals on the attenuation spectrum. For example, if the soil sample solution includes a pH indicator, data captured by the detector 151a may be used to monitor the pH indicator and ascertain soil pH. As another example, the soil sample solution may include acids and/or reagents to enable the detector 151a to measure the amount of phosphorous or potassium in the soil.

In one embodiment, the light source 152 comprises a dual ultraviolet-visible/near-infrared light bulb, such as a dual tungsten-deuterium bulb. The light source 152 allows independent control of the production of ultraviolet light, visible light and near-infrared light. For example, modification of a tungsten filament in the light source 152 modifies production of light having wavelengths of 320 nanometers or longer ("visible light" and "near-infrared light"), while modification of a deuterium filament in the light source 152 modifies production of light having wavelengths shorter than 400 nanometers ("ultraviolet light" or "UV light").

The light source 152 may include a light source holder (not shown) connected to the window 156, where the light source holder includes an opening enabling the coupling of light (either by an optical fiber or by free-space optics) to the window 156. For example, an optical fiber inserted into the opening in the light source holder directs light from the light source 152 through the optical fiber to the window 156.

Light emitted from the light source 152 travels an optical path length from the window 156 covering light source 152 to the window 155 covering detector 151a. The optical path length affects the amount of light captured by a detector 151. Thus, modifying the distance between window 156 and window 155 affects the amount of visible or ultraviolet light absorbed by the soil sample solution in the measurement cell. In one embodiment, the optical path length between windows 156 and 155 is one millimeter.

Windows 156 and 155 isolate the source 152 and detectors 151 from the soil sample solution present in the cavity 154. Windows 156 and 155 have a high transmission of infrared, ultraviolet and visible light. For example, windows 156 and 155 may include quartz or fused-silica windows. In one embodiment, the windows 156 and 155 include a hydrophilic film, such as a film of silicon dioxide, to reduce the likelihood of air bubbles developing near the windows. Alternatively the windows 156 and 155 are made from a hydrophilic material. In one embodiment, the windows 156 and 155 include a non-stick coating such as a TEFLON coating.

In one embodiment, cavity 154 is sloped in order to prevent the occurrence of surface effects on windows 156 and 155. The cavity 154 may, for example, be slanted (e.g., angled) or curved. The slope mitigates the kinetic energy of the soil sample solution that has been filtered by the filtration system 140, thereby inhibiting the creation of surface effects on windows 156 and 155. As a consequence, windows 156 and 155 are more likely to be uniformly covered by a soil sample solution. This improves the optical measurement of soil characteristics, by creating a more consistent optical path for light that is transmitted or reflected by the soil sample solution.

The measurement cell 150 additionally includes an output port 157 for clearing the contents of the measurement cell 150. The output port 157 may additionally be used to input cleaning fluid to provide backpressure to clean the measurement cell 150 and/or the filtration system 140. To perform cleaning, the output port 157 may be coupled to a pneumatic piston or a solenoid valve.

In one embodiment, the soil analysis device 100 may includes a number of measurement cells 150 allowing the measurement of different characteristics of the soil sample simultaneously. For example, a second measurement cell may be used to measure soil pH concurrently with the measurement of other soil nutrients.

In addition to measurements performed by the measurement cell 150, the soil analysis device 100 may also include additional measurement devices in mixing chamber 110 for performing further measurements of the soil sample. Examples of measurement devices include a conductivity probe, a glass pH electrode, and ion selective electrodes including membranes for measuring various nutrients such as nitrate and potassium. The additional measurement devices may also determine a moisture content of a soil sample, a viscosity of the soil sample or the soil sample solution, the temperature of the soil sample or the soil sample solution, or any other suitable characteristics of the soil sample or the soil sample solution. The data determined by the additional measurement devices may be combined with the attenuation spectrum determined by the detector 151 to increase the accuracy of nutrient identification in the soil sample. For example, determining the moisture content of the soil sample allows improvement of a nitrate-nitrogen measurement by subtracting the weight of moisture in the soil sample from the weight of the soil sample. In one embodiment, an additional measurement device captures optical reflectivity measurements of the soil in the mixing chamber 110, before extractant mixing, in the UV, visible, near IR and/or mid IR spectra. The reflectivity of dry soil as a function of wavelength may be correlated to soil type. Such information can be used, in conjunction with the other embodiments discussed herein to provide data about soil characteristics or to refine the measurement of soil characteristics in the measurement cell 150.

The soil analysis device 100 allows for near real-time analysis of soil components by integrating mixing of a soil sample and extractant with analysis of the resulting soil sample solution. For example, the soil measurement of interest is often a final value after all relevant nutrients in the soil have been extracted from the soil sample solution, which may take a significant amount of time. By integrating a high-speed measurement (typically less than 1 second per measurement) measurement cell 150 and coupling it to the mixing chamber 110, the measurement can be performed by the measurement cell 150 many times as the nutrient is being extracted and as the soil sample solution filters through the filtration system 140, allowing the final value of the nutrient to be accurately extrapolated in a much shorter amount of time. In contrast, conventional techniques of soil measurement are time-intensive because they rely on discrete steps of pre-processing the soil, extracting nutrients and then measuring nutrients, preventing these conventional methods from obtaining multiple measurements of soil characteristics during the measurement process.

The flow through rate of the filtration system 140 may be slow enough that air bubbles may occasionally become trapped in between drops of soil sample solution arriving in the measurement cell 150 from the filtration system 140. The air bubbles cause the filtering soil sample solution to become backed up, and can alter measurements of the soil sample solution. To prevent this, in one embodiment the measurement cell 150 includes an overflow line (not shown) before the cavity 154. The overflow line allows trapped air bubbles to escape, allowing filtered soil sample solution to take their place instead. The overflow line is positioned proximately to the filtration system 140 above, vertically, the measurement cell 150 to allow the air to escape.

The overflow line also provides a place where filtered soil sample solution may go once the measurement cell 150 has filled with filtered soil sample solution. The overflow line thus removes excess filtered soil sample solution that is not needed for measurement.

In an alternative embodiment, the shape of the measurement cell 150 may be modified into a "V" shape by adding an upward sloping overflow line at the bottom point of the cavity 154. In this embodiment, the overflow line slopes in a different direction than the input to cavity 154, forming the V-shape. The second portion of the V-shape is formed by the overflow line, allowing trapped air bubbles and excess filtered soil sample solution to escape from the measurement cell 150. In this embodiment, the other elements of the measurement cell 150 such as the light source 152, detector(s) 151, and windows 156 and 155 may be located out-of-plane from the V-shape. The output port 157 may be located at the bottom of the V-shape next to cavity 154.

Measurement of Soil Characteristics

Figure 7:
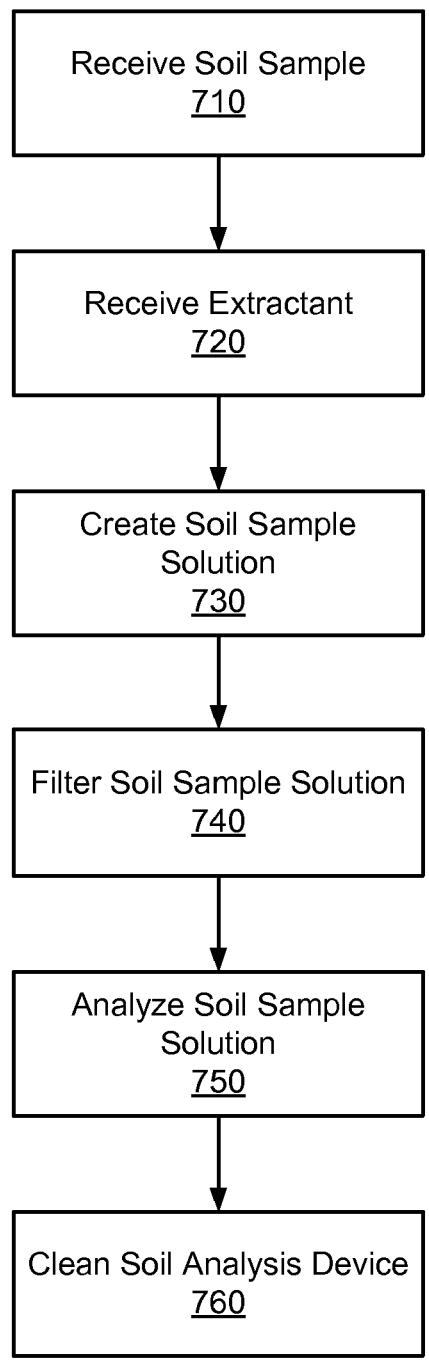
FIG. 7 is a flow chart of a method for analyzing soil sample solutions, according to one embodiment.

FIG. 7 is a flow chart of one embodiment of a method 700 for measuring data describing soil composition using the soil analysis device 100. In the embodiment shown by FIG. 6, the mixing chamber 110 receives 710 a soil sample having a known weight and moisture content. The mixing chamber 110 also receives 720 an extractant. In one embodiment, a volume or weight of extractant is received 720 based on the weight and moisture content of the soil sample to provide a desired ratio of soil to extractant. The mixing chamber 110 may also receive a salt to act as a flocculent on the soil sample.

The contents of the mixing chamber 110 are mixed to create 730 a soil sample solution. A portion of the soil sample solution flows from the mixing chamber 110 into filtration system 140. The filtration system 140 filters 740 the soil sample solution to remove soil particulates, organic matter, and other soluble organic materials from the soil sample solution. For example, the filtration system 140 may perform the steps described with reference to FIGS. 3 and 4 to pressure filter the soil sample solution (slurry) to generate filtrate for analysis. The filtered soil sample solution enters measurement cell 150.

Once in the measurement cell 150, the filtered soil sample solution is analyzed 750 to determine the characteristics of the soil sample. In one embodiment, ultraviolet, visible, and/or near-infrared light are incident upon and at least partially absorbed by the soil sample solution. An attenuation spectrum is measured that provides data regarding how the soil sample solution absorbs different wavelengths of light. Peaks in the attenuation spectrum associated with the soil sample solution allow identification of nutrients, or other components, in the soil sample. A reflection spectrum may also be measured using the light reflected from the soil sample in the measurement cell 150. After measurement, soil analysis device 100 is cleaned 760 to remove the soil sample solution from the mixing chamber 110, filtration system 140, and/or measurement cell 150.

Figure 8:
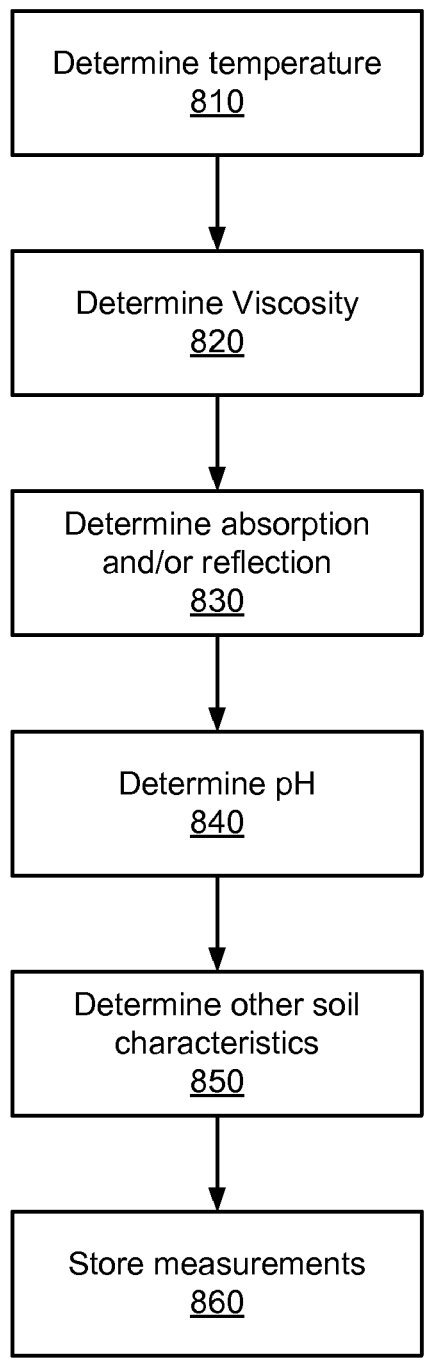
FIG. 8 is a flow chart of a method for capturing multiple types of measurements to determine soil composition, according to one embodiment.

FIG. 8 is a flow chart of one embodiment of a method for analyzing 750 multiple characteristics of a soil sample solution to determine soil sample characteristics. In one embodiment, one or more additional measurement cells 150 are coupled to the mixing chamber 110 and measure various characteristics of a soil sample solution. In one embodiment, measurement cell 150 and one or more additional measurement devices measure various characteristics of the soil sample and the soil sample solution. In one embodiment, measurements of various characteristics of the soil sample solution are measured in a single measurement cell 150, where the contents of the measurement cell 150 may change between measurements for a single soil sample. For example, the soil to extractant ratio may be changed through the addition of additional extractant between measurements, or additional chemicals may be added to perform additional measurements.

In one embodiment, a thermal measurement device determines 810 a temperature of a portion of the soil sample solution. A power detector determines 820 a viscosity of the soil sample solution by measuring the power consumed by the motor in mixing chamber 110 to reach a specified speed, or by measuring the speed of the motor when a fixed amount of power is applied to the motor. In one embodiment, the measurement cell 150 is used to determine 830 an absorption and/or a reflection spectrum of the soil sample solution. In one embodiment an additional measurement device or an additional measurement cell 150 in conjunction with an added chemical determines 840 the pH of the soil.

The temperature, viscosity, attenuation spectrum and pH represent characteristics of the soil. These measurements may also be analyzed to determine other characteristics of the soil that were not directly measured. For example, the temperature, viscosity, attenuation spectrum and pH may be communicated from the soil analysis device 110 to a processor or computing device (not shown) which determines 850 the nutrients present in the soil sample. The measured and determined characteristics of the soil sample are stored 860 in a memory and/or displayed to a user.

In one embodiment, the soil analysis device 100 is used in conjunction with a process for measuring soil characteristics as described in U.S. patent application Ser. No. 13/231,701, filed on Sep. 13, 2011, the subject matter of which is incorporated herein by reference in its entirety.

Hence, the disclosed soil analysis device 100 improves the accuracy of identifying nutrients in a soil sample while also increasing the speed with which the nutrients included in a soil sample are identified.

ADDITIONAL CONSIDERATIONS

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. It should be understood that these terms are not intended as synonyms for each other. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the invention. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a method for automatically identifying characteristics of the composition of a soil sample through the disclosed principles herein. Thus, while particular embodiments and applications have been illustrated and described, it is to be understood that the present invention is not limited to the precise construction and components disclosed herein and that various modifications, changes and variations which will be apparent to those skilled in the art may be made in the arrangement, operation and details of the method and apparatus of the present invention disclosed herein without departing from the spirit and scope of the invention as defined in the appended claims.

What is claimed is:

1. A filtration system of a soil analysis device, the filtration system comprising:
   a chamber including a liquid mixture inlet and a filtrate drain;
   a filter configured to remove particulates from a liquid mixture received from the liquid mixture inlet to generate a filtered liquid mixture, the filter oriented in a substantially vertical orientation and partitioning the chamber into a first chamber configured to receive the liquid mixture from the liquid mixture inlet and a second chamber configured to receive the filtered liquid mixture from the filter and provide the filtered liquid mixture to the filtrate drain, the filter including a perforated area located below the liquid mixture inlet and above the filtrate drain; and
   a pressure source configured to create a pressure differential between the first chamber and the second chamber.

2. The filtration system of claim 1, wherein the filter includes a non-perforated area located above the perforated area.

3. The filtration system of claim 1, wherein the filter includes a non-perforated area located below the perforated area.

4. The filtration system of claim 1, wherein the perforated area is located in a central region of the filter.

5. The filtration system of claim 1, wherein the perforated area extends the full width of the filter.

6. The filtration system of claim 1, wherein the liquid mixture inlet is located at a top of the first chamber.

7. The filtration system of claim 1, wherein the filtrate drain is located at a bottom of the second chamber.

8. The filtration system of claim 1, further comprising a liquid mixture drain located at a bottom of the first chamber.

9. The filtration system of claim 8, further comprising a valve configured to selectively open and close the liquid mixture drain.

10. The filtration system of claim 8, wherein the liquid mixture drain is larger in size than the filtrate drain.

11. The filtration system of claim 1, further comprising a cleaner inlet located at a top of the second chamber.

12. The filtration system of claim 11, wherein the liquid mixture inlet is larger in size than the cleaner inlet.

13. The filtration system of claim 11, wherein the cleaner inlet is coupled to a cleaning fluid container containing a cleaning fluid.

14. The filtration system of claim 13, wherein the pressure source is configured to force the cleaning fluid through the filter to dislodge particulates caught in the filter.

15. The filtration system of claim 1, wherein the pressure source includes an air source coupled to at least one of the first chamber or the second chamber for forcing the liquid mixture through the filter by creating the pressure differential across the filter.

16. The filtration system of claim 15, wherein the air source is either:
   coupled to the first chamber and is configured to increase the pressure in the first chamber to force the liquid mixture through the filter; or
   coupled to the second chamber and is configured to create a vacuum in the second chamber to force the liquid mixture through the filter.

17. The filtration system of claim 1, further comprising a measurement cell coupled to the filtrate drain and configured to analyze the filtered liquid mixture.

18. The filtration system of claim 17, wherein the measurement cell comprises a light source and one or more optical detectors for measuring at least one of an attenuation of light generated by the light source and passing through the filtered liquid mixture or a reflection spectrum of light generated by the light source and passing through the liquid mixture.

19. The filtration system of claim 1, wherein the liquid mixture comprises a portion of a soil sample mixed with an extractant.

20. A method comprising:
   receiving, in a first chamber of a soil analysis device, a liquid mixture from a liquid mixture inlet;
   generating a pressure differential across a filter separating the first chamber from a second chamber of the soil analysis device, the pressure differential causing the liquid mixture in the first chamber to pass through a perforated area of the filter located below the liquid mixture inlet and above a filtrate drain of the second chamber, the filter configured to remove particulates from the liquid mixture to create a filtered liquid mixture received in the second chamber; and
   analyzing the filtered liquid mixture using a measurement cell coupled to the filtrate drain.

* * * * *